United States Patent [19]

Urano et al.

[11] Patent Number: 5,026,880
[45] Date of Patent: Jun. 25, 1991

[54] METHOD FOR PRODUCTION OF 1,3-DIOXOLANES

[75] Inventors: Yoshiaki Urano, Kawasaki; Yukio Kadono, Yokohama, both of Japan

[73] Assignee: Nippon Shokubai Kagaku Kogyo Co., Ltd., Osaka, Japan

[21] Appl. No.: 564,742

[22] Filed: Aug. 9, 1990

[30] Foreign Application Priority Data

Aug. 15, 1989 [JP] Japan ................. 1-209596

[51] Int. Cl.$^5$ ........................... C07D 317/12
[52] U.S. Cl. ................................. 549/430
[58] Field of Search ......................... 549/430

[56] References Cited

U.S. PATENT DOCUMENTS 3,725,438 4/1973 Barone et al. ................. 549/430
4,159,347 6/1979 Yoshida et al. ................ 549/430

Primary Examiner—Nicky Chan
Attorney, Agent, or Firm—Burns, Doane, Swecker & Mathis

[57] ABSTRACT

A method for the production of a 1,3-dioxolane represented by the general formula III:

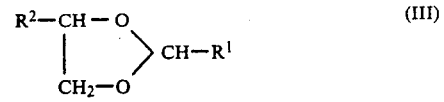

wherein $R^1$ is hydrogen atom or an alkyl group of 1 to 5 carbon atoms and $R^2$ is hydrogen atom or an alkyl group of 1 to 2 carbon atoms or a phenyl group, which method comprises reacting an aldehyde represented by the general formula I

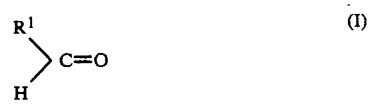

wherein $R^1$ has the same meaning as defined above, with an alkylene oxide represented by the general formul II:

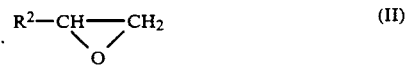

wherein $R^2$ has the same meaning as defined above, in an alkylene glycol solvent corresponding to said alkylene oxide in the presence of at least one catalyst selected from the group consisting of bromides of alkali metals, iodides of alkali metals, bromides of alkaline earth metals, and iodides of alkaline earth metals.

10 Claims, No Drawings

METHOD FOR PRODUCTION OF 1,3-DIOXOLANES

BACKGROUND OF THE INVENTION

1. Field of the Invention

This invention relates to a novel method for the production of 1,3-dioxolanes useful as a solvent, an intermediate for medicines, and a raw material for acetal resin, for example.

2. Description of the Prior Art

In the conventional methods for the production of 1,3-dioxolanes, the method resorting to the cyclization of a glycol with an aldehyde or a ketone and the method resorting to the cyclization of an alkylene oxide with an aldehyde or a ketone have been known.

As respects the production of a 1,3-dioxolane by the cyclization of a glycol with an aldehyde, it is disclosed in DE-A-1914209 (1970), for example, that the reaction of a glycol with an aqueous solution of formaldehyde in the presence of an acid catalyst produces a 1,3-dioxolane containing 7% by weight of water in a yield of 96.5%.

In JP-A No. 49-62469 (1974), it is disclosed that a 1,3-dioxolane of high purity is obtained by reacting a glycol with paraformaldehyde in the presence of an acid catalyst, adding cyclohexane to the reaction mixture and distillating the resultant mixture.

Then, in Ind. Eng. Chem., 46, 787 (1954), it is disclosed that a 1,3-dioxolane of high purity having only a small water content is obtained by reacting a glycol with paraformaldehyde in the presence of an acid catalyst, adding common salt to the reaction distillate thereby inducing separation of the solution into two phases, and rectifying the organic phase.

In the methods which use such glycols and aldehydes as mentioned above as raw materials, however, since the produced 1,3-dioxolanes form azeotropes with water, the separation and removal of water from such 1,3-dioxolanes cannot be easily attained solely by the step of distillation. The production of a 1,3-dioxolane having high purity and a low water content calls for further steps of purification such as extraction and a salting-out treatment and, therefore, tends to boost the cost of production.

As regards the production resorting to the reaction of an alkylene oxide with an aldehyde, it is disclosed in Ber., 74, 145 (1941) and J. Am. Chem. Sec., 55, 3741 (1933) that a 1,3-dioxolane is obtained in a yield of 22 to 63% by performing the reaction in the presence of stannic chloride. It is disclosed in Ann., 710, 85 (1967) that this reaction, when performed in the presence of a quaternary ammonium salt as a catalyst, produces a 1,3-dioxolane in a yield of 36 to 85%.

The methods of production disclosed in these articles of literature, however, have not been fully developed to the extent of finding commercial utility because they have problems of insufficient yield of reaction, difficulty in recovery of used catalyst for re-use, and short service life of catalyst in spite of their freedom from the problem of dehydration of the produced 1,3-dioxolanes.

An object of this invention, therefore, is to provide a novel method for the production of a 1,3-dioxolane.

Another object of this invention is to provide a novel method for producing a 1,3-dioxolane of high purity having only a small water content in a high yield easily solely by a step of distillation.

SUMMARY OF THE INVENTION

These objects are accomplished by a method for the production of a 1,3-dioxolane represented by the general formula III:

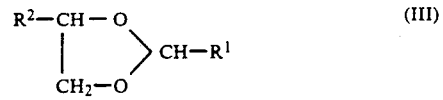

wherein $R^1$ is hydrogen atom or an alkyl group of 1 to 5 carbon atoms and $R^2$ is hydrogen atom or an alkyl group of 1 or 2 carbon atoms or a phenyl group, which method comprises reacting an aldehyde represented by the general formula I:

wherein $R^1$ has the same meaning as defined above, with an alkylene oxide represented by the general formula II:

wherein $R^2$ has the same meaning as defined above, in an alkylene glycol solvent corresponding to the alkylene oxide in the presence of at least one catalyst selected from the group consisting of bromides of alkali metals, iodides of alkali metals, bromides of alkaline earth metals, and iodides of alkaline earth metals.

In the method of the present invention for the production of a 1,3-dioxolane by the reaction of an aldehyde with an alkylene oxide, since an alkylene glycol corresponding to the alkylene oxide is used as a solvent and a bromide compound or an iodide compound of an alkali metal and/or an alkaline earth metal is used as a catalyst, the 1,3-dioxolane aimed at can be produced economically advantageously in a high yield with an easy procedure of purification. Particularly, the reaction mixture which is formed in the method of this invention contains only a minute amount of water even when a water-containing aldehyde is used as a raw material. Thus, the method of this invention manifests an outstanding effect of enabling a 1,3-dioxolane of high purity to be produced exclusively by a treatment of distillation without entailing any step for the removal of water.

EXPLANATION OF THE PREFERRED EMBODIMENT

The aldehydes represented by the general formula I:

$$\underset{H}{\overset{R^1}{\diagdown}}C=O \qquad (I)$$

wherein $R^1$ is hydrogen atom or an alkyl group of 1 to 5 carbon atoms, preferably hydrogen atom or an alkyl group of 1 to 2 carbon atoms, and most preferably hydrogen atom include formaldehyde, acetaldehyde, propionaldehyde, butylaldehyde, valeraldehyde, hexylaldehyde, and polymers thereof, i.e. paraformaldehyde and paraldehyde, for example.

The alkylene oxides represented by the general formula II:

wherein $R^2$ is hydrogen atom, an alkyl group of 1 or 2 carbon atoms, or a phenyl group, preferably hydrogen atom or methyl group, and most preferably hydrogen atom, include ethylene oxide, propylene oxide, butylene oxide, and styrene oxide, for example.

The alkylene glycols which are usable as a reaction solvent in the present invention include ethylene glycol, propylene glycol, butylene glycol, and phenyl ethylene glycol, for example. Particularly when a water-containing aldehyde is used as a raw material, it is optimum to use as a reaction solvent an alkylene glycol which is obtained by the reaction of hydration of an alkylene oxide being used as a raw material.

The bromides and iodides of alkali metals and/or alkaline earth metals which are usable as a catalyst in this invention include sodium bromide, potassium bromide, sodium iodide, potassium iodide, calcium bromide, magnesium bromide, calcium iodide, and magnesium iodide, for example. Among other catalysts cited above, iodides or bromides of alkali metals probe to be more preferable. Particularly, results preferable in terms of reaction yield and reaction velocity are obtained when potassium iodide is used as a catalyst.

The 1,3-dioxolanes which can be produced in the present invention include 1,3-dioxolane, 2-methyl-1,3-dioxolane, 2-ethyl-1,3-dioxolane, 2-propyl-1,3-dioxolane, 2-butyl-1,3-dioxolane, 2-pentyl-1,3-dioxolane, 4-methyl-1,3-dioxolane, 2-methyl-4-methyl-1,3-dioxolane, 2-ethyl-4-methyl-1,3-dioxolane, 2-propyl-4-methyl-1,3-dioxolane, 2-butyl-4-methyl-1,3-dioxolane, 2-pentyl-4-methyl-1,3-dioxolane, 4-ethyl-1,3-dioxolane, 2-methyl-4-ethyl-1,3-dioxolane, 2-ethyl-4-ethyl-1,3-dioxolane, 2-propyl-4-ethyl-1,3-dioxolane, 2-butyl-4-ethyl-1,3-dioxolane, 2-pentyl-4-ethyl-1,3-dioxolane, 4-phenyl-1,3-dioxolane, 2-methyl-4-phenyl-1,3-dioxolane, 2-ethyl-4-phenyl-1,3-dioxolane, 2-propyl-4-phenyl-1,3-dioxolane, 2-butyl-4-phenyl-1,3-dioxolane, and 2-pentyl-4-phenyl-1,3-dioxolane, for example.

In the method of this invention for the production of 1,3-dioxolanes, the amount of the catalyst to be used is preferable to be in the range of 0.01 to 10 mol %, more preferably 0.1 to 5 mol %, based on the amount of the aldehyde represented by the general formula I. If this amount is less than 0.01 mol %, the reaction is impracticable because the reaction velocity is unduly low. Conversely, if this amount exceeds 10 mol %, the reaction is not advantageous economically because the cost of catalyst is unduly high. After the completion of the reaction, the catalyst remains in the solvent from which the produced 1,3-dioxolane has been separated by distillation. The catalyst need not be separated and recovered from the solvent but may be used repeatedly in the reaction as contained in the solvent.

For the method of this invention, the use of the solvent is indispensable. If the solvent is not used, the reaction pressure must be increased to a high level even exceeding 20 kg/cm$^2$ when ethylene oxide or propylene oxide, for example, is used and the reaction velocity is low and the yield is low as well.

The amount of the solvent to be used is only required to be enough for dissolving the catalyst. Generally, it is in the range of 30 to 200% by weight, based on the amount of the aldehyde to be used.

To obtain 1,3-dioxolanes in a high yield, the amount of the alkylene oxide to be used is in the range of 1 to 2 mols per mol of the aldehyde to be used. When a water-containing aldehyde such as formalin, paraformaldehyde, or acetaldehyde is used as aldehyde, one of the raw materials herein, it is advantageous to use the alkylene oxide in an amount in the range of 1 to 2 times the total number of mols of the aldehyde and water. In this case, since the water contained in the aldehyde reacts with the alkylene oxide and consequently transforms into an alkylene glycol, 1,3-dioxolanes of high purity having a water content of not more than 0.1% by weight can be obtained by performing only a treatment of distillation after the reaction. Though the by-produced alkylene glycol can be used in its unmodified form as a solvent for the reaction of this invention, it may be separated by distillation and used for some other purpose.

In the method of this invention for the production of 1,3-dioxolanes, the reaction temperature is preferable to be in the range of 50° to 150° C., preferably 80° to 120° C. If this temperature is lower than 50° C., the reaction suffers from poor productivity because the reaction time is unduly extended. If the temperature exceeds 150° C., the reaction tends to entail side-reaction and suffer from a decline of yield. The reaction pressure is only required to be enough for dissolving the raw materials, i.e. an alkylene oxide and an aldehyde. It may be normal pressure or increased pressure. Generally, the reaction is preferable to be performed under application of a pressure in the range of 2 to 10 kg/cm$^2$, preferably 5 to 10 kg/cm$^2$.

In the present invention, the method for the production of 1,3-dioxolanes can be carried out in the form of a batchwise, semibatchwise, or continuous operation.

One typical procedure to be employed for executing the method of this invention for the production of 1,3-dioxolanes comprises charging a pressure proof reaction vessel with prescribed amounts of an aldehyde, an alkylene glycol, and a catalyst, displacing the internal gas of the reaction system with nitrogen, then heating the contents of the reaction vessel to a temperature in the range of 60° to 150° C., introducing an alkylene oxide into the interior of the reaction vessel under a prescribed pressure until a prescribed total amount, allowing the resultant reaction mixture to age for a period in the range of 1 to 10 hours, preferably 2 to 5 hours thereby completing the reaction, and thereafter separating the produced 1,3-dioxolanes as by distillation. Consequently, there is obtained 1,3-dioxolanes of high purity in a high yield. The residue of the distillation which contains the catalyst can be used repeatedly as the reaction solvent.

The following examples are cited exclusively for the purpose of illustration of this invention. It should be noted that these examples do not limit the scope of the present invention in any respect.

EXAMPLE 1

In an autoclave of stainless steel provided with a stirrer, 192 g of paraformaldehyde (formaldehyde content 78% by weight) having a water content of 17% by weight, 17 g of potassium iodide, and 192 g of ethylene glycol were placed. The air in the gaseous phase inside the autoclave was displaced with nitrogen and the interior of the autoclave was compressed with nitrogen to 2.0 kg/cm$^2$. The mixture in the autoclave was heated to 105° C. and 302 g of ethylene oxide was introduced therein over a period of 6 hours. At that time, the inner pressure gradually rose and finally reached 7 kg/cm$^2$. During the introduction of the ethylene oxide, the temperature of the mixture remained at 105° C. The reaction mixture was left aging at 105° C. for 1 hour and then cooled to room temperature.

The reaction mixture, on analysis, was found to have a water content of not more than 0.005% by weight and a formaldehyde content of not more than 0.01% by weight and contain 353 g of 1,3-dioxolane and 115 g of formed ethylene glycol.

The yield of 1,3-dioxolane was 95.5 mol % based on formaldehyde and 69.6 mol % based on ethylene oxide. The yield of ethylene glycol was 27.1 mol % based on ethylene oxide.

EXAMPLE 2

In an autoclave of stainless steel provided with a stirrer, 160 g of paraformaldehyde (formaldehyde content 94% by weight) having a water content of 3% by weight, 17 g of potassium iodide, and 160 g of ethylene glycol were placed. The air in the gaseous phase inside the autoclave was displaced with nitrogen and the interior of the autoclave was compressed with nitrogen to 2.0 kg/cm$^2$. The mixture was heated to 105° C. and 232 g of ethylene oxide was introduced therein over a period of 6 hours. At that time, the pressure gradually rose and finally reached 6.5 kg/cm$^2$. During the introduction of the ethylene oxide, the mixture remained at 105° C. Then, the reaction mixture was left aging at 105° C. for 1 hour and then cooled to room temperature.

The reaction mixture, on analysis, was found to have a water content of not more than 0.005% by weight and a formaldehyde content of not more than 0.01% by weight and contain 349 g of 1,3-dioxolane and 17 g of formed ethylene glycol.

The yield of 1,3-dioxolane was 94.2 mol % based on formaldehyde and 89.3 mol % based on ethylene oxide. The yield of ethylene glycol was 5.2 mol % based on ethylene oxide.

EXAMPLE 3

In an autoclave of stainless steel provided with a stirrer, 160 g of paraformaldehyde (formaldehyde content 94% by weight) having a water content of 3% by weight, 8 g of potassium bromide, and 160 g of ethylene glycol were placed. The air in the gaseous phase inside the autoclave was displaced with nitrogen and the interior of the autoclave was compressed with nitrogen to 2.0 kg/cm$^2$. The mixture was heated to 105° C. and 232 g of ethylene oxide was introduced therein over a period of 12 hours. At that time, the pressure gradually rose and finally reached 6.5 kg/cm$^2$. During the introduction of the ethylene oxide, the mixture remained at 105° C. Then, the reaction mixture was left aging at 105° C. for 1 hour and then cooled to room temperature.

The reaction mixture, on analysis, was found to have a water content of not more than 0.005% by weight and a formaldehyde content of not more than 1.0% by weight and contain 334 g of 1,3-dioxolane and 17 g of formed ethylene glycol.

The yield of 1,3-dioxolane was 90.2 mol % based on formaldehyde and 85.6 mol % based on ethylene oxide. The yield of ethylene glycol was 5.2 mol % based on ethylene oxide.

EXAMPLE 4

In an autoclave of stainless steel provided with a stirrer, 160 g of paraformaldehyde (formaldehyde content 94% by weight) having a water content of 3% by weight, 17 g of potassium iodide, and 160 g of propylene glycol were placed. The air in the gaseous phase inside the autoclave was displaced with nitrogen and the interior of the autoclave was compressed with nitrogen to 2.0 kg/cm$^2$. The mixture was heated to 105° C. and 307 g of propylene oxide was introduced therein over a period of 7 hours. At that time, the pressure gradually rose and finally reached 6.0 kg/cm$^2$. During the introduction of the propylene oxide, the mixture remained at 105° C. Then, the reaction mixture was left aging at 105° C. for 2 hours and then cooled to room temperature.

The reaction mixture, on analysis, was found to have a water content of not more than 0.005% by weight and a formaldehyde content of 1.2% by weight and contain 396 g of 4-methyl-1,3-dioxolane and 21 g of formed propylene glycol.

The yield of 4-methyl-1,3-dioxolane was 90.0 mol % based on formaldehyde and 85.3 mol % based on propylene oxide. The yield of propylene glycol was 5.2 mol % based on propylene oxide.

EXAMPLE 5

In an autoclave of stainless steel provided with a stirrer, 240 g of acetaldehyde (acetaldehyde 92% by weight) having a water content of 6% by weight, 17 g of potassium iodide, and 120 g of ethylene glycol were placed. The air in the gaseous phase inside the autoclave was displaced with nitrogen and the interior of the autoclave was compressed with nitrogen to 2.0 kg/cm$^2$. The mixture was heated to 105° C. and 256 g of ethylene oxide was introduced therein over a period of 7 hours. At that time, the pressure gradually rose and finally reached 7.0 kg/cm$^2$. During the introduction of the ethylene oxide, the mixture remained at 105° C. Then, the reaction mixture was left aging at 105° C. for 2 hours and then cooled to room temperature.

The reaction mixture, on analysis, was found to have a water content of not more than 0.005% by weight and an acetaldehyde content of not more than 0.01% by weight and contain 411 g of 2-methyl-1,3-dioxolane and 50 g of formed ethylene glycol.

The yield of 2-methyl-1,3-dioxolane was 93.3 mol % based on acetaldehyde and 80.2 mol % based on ethylene oxide. The yield of ethylene glycol was 14.0 mol % based on ethylene oxide.

In an autoclave of stainless steel provided with a stirrer, 192 g of paraformaldehyde (formaldehyde content 78% by weight) having a water content of 17% by weight and 17 g of potassium iodide were placed. The air in the gaseous phase inside the autoclave was displaced with nitrogen and the interior of the autoclave was compressed with nitrogen to 2.0 kg/cm$^2$. The mixture was heated to 105° C. and 20 g of ethylene oxide was introduced therein. At that time, the pressure suddenly rose and finally reached 10 kg/cm$^2$. The introduction of the ethylene oxide was discontinued. The mixture remained at 105° C. No fall of the pressure was observed 1 hour after the stop of the ethylene oxide introduction. The reaction mixture was cooled to room temperature.

The reaction mixture showed substantially no sign of formation of 1,3-dioxolane.

REFERENTIAL EXAMPLE 1

In a distillation apparatus provided with a distillation column packed with Dickson packings 3 mm in diameter to a height of 40 cm, the reaction mixture obtained in Example 1 was subjected to normal pressure distillation at a reflux ratio of 3. After the volatile component was separated by distillation, there was obtained 335 g of 1,3-dioxolane of purity of not less than 99% having a water content of not more than 0.005% by weight at boiling temperatures in the range of 74° to 76° C. In this case, the yield of 1,3-dioxolane by distillation was 95%.

REFERENTIAL EXAMPLE 2

In a distillation apparatus provided with distillation column packed with Dickson packings 3 mm in diameter to a height of 40 cm, the reaction mixture obtained in Example 5 was subjected to normal pressure distillation in the same manner as in Referential Example 1. After the volatile component was separated by distillation, there was obtained 386 g of 2-methyl-1,3-dioxolane of purity of not less than 99% having a water content of not more than 0.005% by weight at boiling points in the range of 82° to 83° C. In this case, the yield of 2-methyl-1,3-dioxolane by distillation was 94%.

What is claimed is:

1. A method for the production of a 1,3-dioxolane represented by the general formula III:

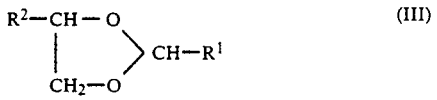

wherein $R^1$ is hydrogen atom or an alkyl group of 1 to 5 carbon atoms and $R^2$ is hydrogen atom or an alkyl group of 1 to 2 carbon atoms or a phenyl group, which method comprises reacting an aldehyde represented by the general formula I

wherein $R^1$ has the same meaning as defined above, with an alkylene oxide represented by the general formula II:

wherein $R^2$ has the same meaning as defined above, in an alkylene glycol solvent corresponding to said alkylene oxide in the presence of at least one catalyst selected from the group consisting of bromides of alkali metals, iodides of alkali metals, bromides of alkaline earth metals, and iodides of alkaline earth metals.

2. A method according to claim 1, wherein the amount of said catalyst is in the range of 0.01 to 10 mol %, based on the amount of an aldehyde represented by the general formula I.

3. A method according to claim 1, wherein the amount of said solvent is in the range of 50 to 200% by weight, based on the amount of said aldehyde.

4. A method according to claim 1, wherein the amount of said alkylene oxide is in the range of 1 to 2 mol per mol of said aldehyde.

5. A method according to claim 1, wherein said reaction is carried out at a temperature in the range of 50° to 150° C.

6. A method according to claim 5, wherein said reaction is carried out under a pressure in the range of 2 to 10 kg/cm².

7. A method according to claim 1, wherein $R^1$ is hydrogen atom or an alkyl group of 1 to 5 carbon atoms and $R^2$ is hydrogen atom, an alkyl group of 1 or 2 carbon atoms, or a phenyl group.

8. A method according to claim 1, wherein $R^1$ is hydrogen atom or an alkyl group of 1 to 2 carbon atoms and $R^2$ is hydrogen atom or methyl group.

9. A method according to claim 1, wherein said catalyst is an iodide or a bromide of an alkali metal.

10. A method according to claim 9, wherein said catalyst is potassium iodide.

* * * * *